(12) United States Patent
Mori et al.

(10) Patent No.: US 11,294,547 B2
(45) Date of Patent: Apr. 5, 2022

(54) QUERY-BASED THREE-DIMENSIONAL ATLAS FOR ACCESSING IMAGE-RELATED DATA

(75) Inventors: Susumu Mori, Ellicott City, MD (US); Michael I. Miller, Towson, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 158 days.

(21) Appl. No.: 14/129,552

(22) PCT Filed: Jun. 28, 2012

(86) PCT No.: PCT/US2012/044611
§ 371 (c)(1),
(2), (4) Date: Feb. 23, 2014

(87) PCT Pub. No.: WO2013/003571
PCT Pub. Date: Jan. 3, 2013

(65) Prior Publication Data
US 2014/0181754 A1 Jun. 26, 2014

Related U.S. Application Data

(60) Provisional application No. 61/608,261, filed on Mar. 8, 2012, provisional application No. 61/502,372, filed on Jun. 29, 2011.

(51) Int. Cl.
*G06F 3/0484* (2013.01)
*G06F 3/0481* (2013.01)
(Continued)

(52) U.S. Cl.
CPC ...... *G06F 3/04842* (2013.01); *G06F 3/04815* (2013.01); *G06F 16/444* (2019.01);
(Continued)

(58) Field of Classification Search
None
See application file for complete search history.

(56) References Cited

U.S. PATENT DOCUMENTS 5,970,499 A * 10/1999 Smith .................. G06F 16/40
6,608,628 B1 * 8/2003 Ross .................... G16H 40/67
345/619

(Continued)

FOREIGN PATENT DOCUMENTS

WO 2011059554 A2 5/2011
WO 2011071363 A2 6/2011

OTHER PUBLICATIONS

Medha V. Wyawahare et al., "Image Registration Techniques: An overview", published in International Journal of Signal Processing, Image Processing and Pattern Recognition, vol. 2, No. 3, Sep. 2009, retrieved Nov. 22, 2021 (Year: 2009).*

(Continued)

*Primary Examiner* — Shourjo Dasgupta
(74) *Attorney, Agent, or Firm* — MH2 Technology Law Group LLP

(57) ABSTRACT

An embodiment in accordance with the present invention provides a system and method for a three-dimensional interface for interacting with a database. The three-dimensional interface can include an interactive three-dimensional atlas depicting an element of anatomy, machine, device, or other object. Given the three-dimensional nature of the atlas, a user can zoom in on particular areas to view them with more specificity. Different structural points of the anatomy are labeled with names or coordinates, such that the user can select one of the structural points and search a database for information related to that specific structural point. The user can also use specific keywords to search with respect to the specific structural point selected. The three-dimensional interface and atlas are displayed to the user on a computing (Continued)

device that can either house the database within its memory or alternately communicate with the database over a network.

21 Claims, 7 Drawing Sheets

(51) Int. Cl.

| | |
|---|---|
| G06F 16/48 | (2019.01) |
| G16H 50/50 | (2018.01) |
| G06F 3/04842 | (2022.01) |
| G06F 3/04815 | (2022.01) |
| G06T 19/00 | (2011.01) |
| G06F 16/44 | (2019.01) |
| G16Z 99/00 | (2019.01) |

(52) U.S. Cl.
CPC .............. *G06F 16/48* (2019.01); *G06T 19/00* (2013.01); *G16H 50/50* (2018.01); *G16Z 99/00* (2019.02); *G06T 2210/41* (2013.01)

(56) References Cited

U.S. PATENT DOCUMENTS

| | | | | |
|---|---|---|---|---|
| 7,646,898 | B1* | 1/2010 | Nowinski | G06T 7/0012 |
| | | | | 382/128 |
| 9,053,562 | B1* | 6/2015 | Rabin | G06F 16/583 |
| 9,092,860 | B2* | 7/2015 | Van Muiswinkel | G06T 7/33 |
| 2002/0103428 | A1* | 8/2002 | deCharms | A61B 5/055 |
| | | | | 600/410 |
| 2002/0103429 | A1* | 8/2002 | deCharms | A61B 5/055 |
| | | | | 600/410 |
| 2003/0013951 | A1* | 1/2003 | Stefanescu | G06F 17/30256 |
| | | | | 600/407 |
| 2004/0210392 | A1* | 10/2004 | Fleury | E21B 47/00 |
| | | | | 702/6 |
| 2005/0063251 | A1* | 3/2005 | Guidry | G01V 1/34 |
| | | | | 367/35 |
| 2005/0171558 | A1* | 8/2005 | Abovitz | A61B 90/36 |
| | | | | 606/130 |
| 2005/0217896 | A1* | 10/2005 | Terentyev | E21B 44/00 |
| | | | | 175/40 |
| 2005/0283053 | A1* | 12/2005 | deCharms | A61B 5/055 |
| | | | | 600/300 |
| 2006/0017749 | A1* | 1/2006 | McIntyre | A61N 1/36082 |
| | | | | 345/664 |
| 2006/0277073 | A1* | 12/2006 | Heilbrunn | G06Q 50/24 |
| | | | | 705/3 |
| 2007/0003124 | A1 | 1/2007 | Wood et al. | |
| 2007/0014459 | A1* | 1/2007 | Palmer | G06T 7/0012 |
| | | | | 382/128 |
| 2007/0127798 | A1* | 6/2007 | Chakraborty | G06F 17/30014 |
| | | | | 382/128 |
| 2007/0244395 | A1* | 10/2007 | Wang | A61B 5/0059 |
| | | | | 600/476 |
| 2008/0143821 | A1* | 6/2008 | Hung | G06T 3/0062 |
| | | | | 348/36 |
| 2008/0188969 | A1* | 8/2008 | O'Malley | G06F 17/50 |
| | | | | 700/97 |
| 2008/0192052 | A1* | 8/2008 | Ljung | G06T 3/4007 |
| | | | | 345/426 |
| 2008/0232658 | A1* | 9/2008 | Sugaya | G06T 7/0012 |
| | | | | 382/128 |
| 2009/0074265 | A1* | 3/2009 | Huang | A61B 1/041 |
| | | | | 382/128 |
| 2009/0156521 | A1* | 6/2009 | Abbracchio | C12N 15/1138 |
| | | | | 514/44 R |
| 2009/0192813 | A1* | 7/2009 | Gejdos | G06F 19/323 |
| 2009/0274352 | A1* | 11/2009 | Chang | G01R 33/5601 |
| | | | | 382/130 |
| 2009/0289937 | A1* | 11/2009 | Flake | G06T 17/05 |
| | | | | 345/419 |
| 2009/0317781 | A1 | 12/2009 | Oosthuizen | |
| 2009/0319388 | A1* | 12/2009 | Yuan | G06Q 30/0601 |
| | | | | 705/26.1 |
| 2010/0223299 | A1* | 9/2010 | Yun | G06F 16/532 |
| | | | | 707/803 |
| 2010/0284585 | A1* | 11/2010 | Wang | G06T 19/00 |
| | | | | 382/128 |
| 2010/0293164 | A1* | 11/2010 | Weese | G06F 19/321 |
| | | | | 707/737 |
| 2010/0322525 | A1* | 12/2010 | Kohli | G06K 9/6297 |
| | | | | 382/226 |
| 2011/0006765 | A1* | 1/2011 | Zhao | G01R 33/4826 |
| | | | | 324/307 |
| 2011/0058733 | A1* | 3/2011 | Inoue | G06K 9/4671 |
| | | | | 382/154 |
| 2011/0103657 | A1* | 5/2011 | Kang | A61B 6/504 |
| | | | | 382/128 |
| 2011/0255765 | A1* | 10/2011 | Carlson | A61B 5/0064 |
| | | | | 382/131 |
| 2011/0289086 | A1* | 11/2011 | Jordan | G06F 17/30303 |
| | | | | 707/737 |
| 2011/0313649 | A1* | 12/2011 | Bales | G01C 21/20 |
| | | | | 701/455 |
| 2012/0035463 | A1* | 2/2012 | Pekar | G06T 7/33 |
| | | | | 600/411 |
| 2012/0146896 | A1* | 6/2012 | Eckl | G06T 1/00 |
| | | | | 345/156 |
| 2012/0150048 | A1* | 6/2012 | Kang | G06T 7/149 |
| | | | | 600/481 |
| 2013/0102877 | A1* | 4/2013 | Mori | A61B 5/055 |
| | | | | 600/410 |
| 2015/0178321 | A1* | 6/2015 | Rivlin | G06F 17/30277 |
| | | | | 707/728 |

OTHER PUBLICATIONS

Guner, O., et al., "Pharmacophore Modeling and Three Dimensional Database Searching for Drug Design Using Catalyst: Recent Advances", Current Medicinal Chemistry, (2004) vol. 11, No. 22, pp. 2991-3005.
Hermone, A., et al., "Three-Dimensional Database Mining Identifies a Unique Chemotype that Unites Structurally Diverse Botulinum Neurotoxin Serotype A Inhibitors in a Three-Zone Pharmacophore", ChemMedChem (2008) vol. 3, pp. 1905-1912.

Martone, M., et al., "The Smart Atlas: Spatial and Semantic Strategies for Multiscale Integration of Brain Data", Anatomy Ontologies for Bioinformatics, Principles and Practice, Jan. 1, 2008, vol. 6, pp. 267-286.

Russell, B., et al., "Building a database of 3D scenes from user annotations", IEEE. Issue Date: Jun. 20-25, 2009.

Sutherland, J., et al., "Pruned Receptor Surface Models and Pharmacophores for Three-Dimensional Database Searching", J. Med. Chem. (2004) vol. 47, No. 15, pp. 3777-3787.

European Search Report dated Apr. 24, 2015 for Application No. 12805170.3.

* cited by examiner

QUERY-BASED THREE-DIMENSIONAL ATLAS FOR ACCESSING IMAGE-RELATED DATA

CROSS-REFERENCE TO RELATED APPLICATIONS

This application is a 35 U.S.C. § 371 U.S. national entry of International Application PCT/US2012/044611, having an international filing date of Jun. 28, 2012, which claims the benefit of U.S. Provisional Application No. 61/502,372, filed Jun. 29, 2011, and U.S. Provisional Application No. 61/608,261, filed Mar. 8, 2012, the content of each of the aforementioned applications is herein incorporated by reference in their entirety.

This application claims the benefit of U.S. Provisional Patent Application Nos. 61/502,272, filed Jun. 29, 2011, and 61/608,261, filed Mar. 8, 2012, which are incorporated by reference herein, in their entirety.

GOVERNMENT SUPPORT

This invention was made with government support under AG 020012; EB 003543; and RR 015241 awarded by the National Institute of Health. The government has certain rights in the invention.

FIELD OF THE INVENTION

The present invention relates generally to information management and dissemination. More particularly, the present invention relates to a three-dimensional interface for interacting with a database.

BACKGROUND OF THE INVENTION

There are numerous anatomical atlas books in the market. Given the limitations of printed media, these atlas books depict an anatomical structure in two-dimensions. These books contain images such as histology and MR, and while these atlases serve research communities well, there are several fundamental limitations. First, the locations and orientations of two-dimensional image panels are limited. If two types of image contrasts, such as different histology staining or MR contrasts, are presented, the number of required panels would double. For example, if there are 120 pages, only 20 slice locations can be shown for two contrasts and three orientation (coronal, sagittal, axial). This is, approximately every 5-10 mm for slice intervals if the atlas is for the brain of approximately 200. In addition, the size of the images is fixed. Even for histology sections, which potentially can provide a view of a very high resolution, if the panel covers the entire anatomical element or an entire structure within the anatomical element, the paper size of approximately 8 to 11 inches, practically determines the magnification and users do not have access to higher magnification views. Namely, regardless of the spatial resolution of the raw data, the deliverable resolution is determined by the pre-determined panel format of the atlas. In addition, many of the existing atlases are based on a series of two-dimensional panels and not real three-dimensional information, which limits the research use beyond reference and education.

Electronic atlases depicting anatomical structures are also available. An exemplary electronic atlas of the brain consists of 69 coronal histology sections with myelin staining and corresponding hand-drawn structural definition maps. The electronic format allows a publisher to include a larger number of panels, than the print media counterpart, with different contrasts. Users can also dynamically control the slices and contrasts of the section as well as magnifications of the section. This atlas is a powerful resource for reference/education and as a database. For instance, Allen Institute human brain atlases are based on post-mortem MRI and are designed for gene mapping but they are still under construction with a limited capability. There are also many non-commercial-based web atlases such as Human Brain Atlas at Michigan State University (www.msu.edu/Home/Atlases) and Whole Brain Atlas (www.med.harvard.edu/aanlib), which are based on MRI and/or histology sections with point-and-annotate labeling. BrainMaps (www.brainmaps.org) also provides two-dimensional panels of various high-resolution histology sections but without coordinates and annotations. None of these atlases, however, provide a multi-scale function with a consistent coordinate system, segmentation, and link to rich multi-content knowledge database.

It would therefore be advantageous to provide a three-dimensional interface for observing and interacting with an element of anatomy as well searching a database for information relevant to a particular portion of the element of anatomy.

SUMMARY OF THE INVENTION

The foregoing needs are met, to a great extent, by the present invention, wherein in one aspect, a system for providing and retrieving information related to a three-dimensional entity includes a three-dimensional atlas depicting the entity, wherein the three-dimensional atlas includes at least one label. The system also includes a database containing the information related to the entity. The information is categorized relative to the labels. An interface for searching the database is configured such that a user can select one of the at least one labels from the three-dimensional atlas to search the database. The interface returns search results categorized relative to the one of the at least one label in the database. The three-dimensional atlas, the database, and the interface are programmed onto at least one computing device.

According to another aspect of the present invention, the entity depicted in the three-dimensional database is an element of anatomy. The three-dimensional atlas includes images such as magnetic resonance imaging (MRI) images, histology images, PET-scan images, and CAT-scan images. The at least one label can be a spatial coordinate or a designation for an anatomical structure. The interface can be configured such that the user can search within the information categorized relative to the at least one label in the database. Additionally, the interface can be configured for the user to perform a keyword search of the database. The database can take the form of a supervised database and an unsupervised database, and the unsupervised database is built from information available on the internet.

According to another aspect of the present invention, a method for searching for information related to an entity includes interacting with a computerized user interface to review a three-dimensional atlas of the entity. The method also includes selecting a label on the computerized user interface corresponding to an area of the three-dimensional atlas of the entity. The method also includes entering a query into the computerized user interface related to the label corresponding to the area of the three-dimensional atlas.

Additionally, the method includes reviewing results related to the query entered into the user-interface.

According to yet another aspect of the present invention the database is disposed on a remote server. Alternately, the database can be disposed on the computerized user interface. The method can further include performing a key-word search related to the label corresponding to the area of the three-dimensional atlas.

According to still another aspect of the present invention, a system for retrieving information related to an organ or tissue includes a three-dimensional atlas depicting the organ or tissue. The three-dimensional atlas includes at least one label, and said three-dimensional atlas is configured for a user to interact. The atlas can also be presented at multiple scales (e.g. cm, mm, and micrometer scales) and different anatomical labels with different anatomical scales can be included in each scale level. The system also includes a database containing the information related to the organs or tissues. The information is categorized relative to the at least one label. An interface for searching the database is configured such that a user can select one of the at least one labels from the three-dimensional atlas to search the database. The interface returns search results categorized relative to the one of the at least one label in the database. The three-dimensional atlas, the database, and the interface are programmed onto at least one computing device.

According to another aspect of the present invention, the three-dimensional atlas includes images, such as, magnetic resonance imaging (MRI) images, histology images, PET-scan images, and CAT-scan images. The at least one label can be a spatial coordinate and/or a designation for a structure within the brain. The interface is configured such that the user can search within the information categorized relative to the at least one label in the database. The database includes a supervised database and an unsupervised database, and the unsupervised database is built from information available on the internet.

The three-dimensional atlas can be used as a three-dimensionally arranged index to search and retrieve various types of written or other types of electronic intellectual properties such as textbooks, journals, pictures, and photographs, in which the intellectual properties are considered as one of the supervised databases. The same three-dimensional atlas can be used as a shared index of multiple intellectual properties. The requested and retrieved information through the 3D atlas can be a portion of the intellectual properties, which will allow transaction of only the requested portion of the intellectual properties. This will facilitate the sharing and selling the intellectual properties in more efficient manner.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and.

DETAILED DESCRIPTION

Figure 1:
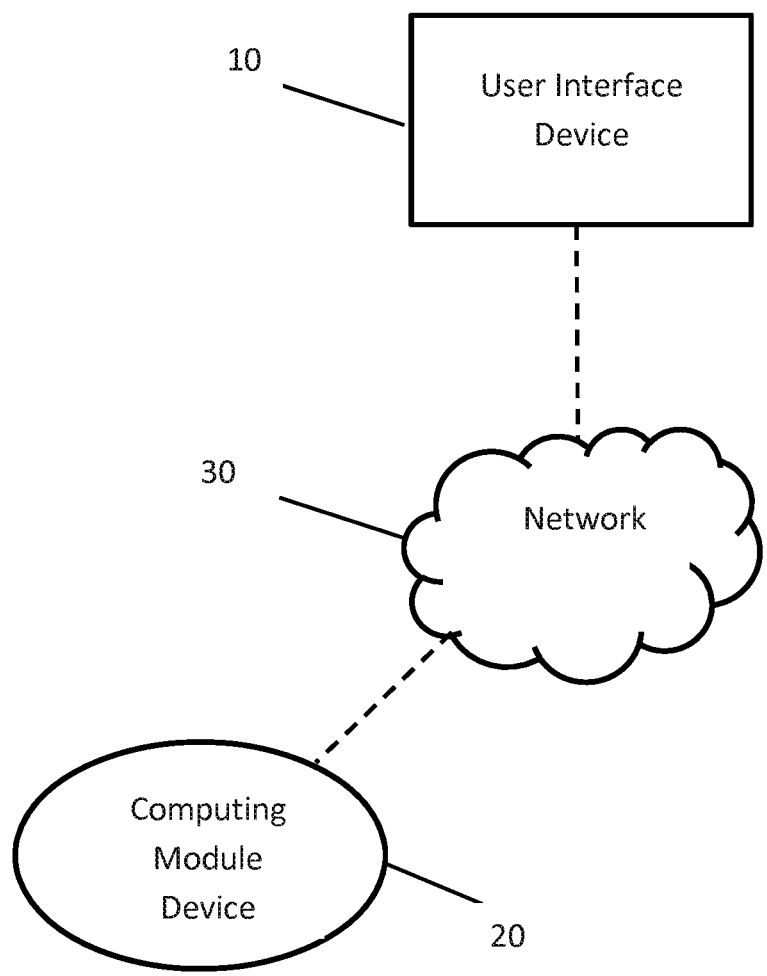
FIG. 1 illustrates a schematic view of a system for interacting with a three-dimensional atlas and database according to an embodiment of the present invention.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides a system and method for a three-dimensional interface for interacting with a database. The three-dimensional interface can include an interactive three-dimensional atlas depicting an element of anatomy, machine, device, or other object. Given the three-dimensional nature of the atlas, a user can zoom in on particular areas to view them with more specificity. Different structural points of the anatomy are labeled with names or coordinates, such that the user can select one of the structural points and search a database for information related to that specific structural point. The user can also use specific keywords to search with respect to the specific structural point selected. The three-dimensional interface and atlas are displayed to the user on a computing device that can either house the database within its memory or alternately communicate with the database over a network.

The three-dimensional electronic atlas, according to the present invention, can serve as a portal with three-dimensionally arranged labels (key words), which are connected to databases available in the local computer, as well as the Internet. For the Internet-based databases, a centralized server can host such a database and atlases will serve as a portal to retrieve information from the centralized server upon request. In addition, the three-dimensional electronic atlas will create an efficient and unique distribution method of intellectual properties, such as textbooks, by transferring only the requested sections related to the anatomical entity of interest. This architecture reduces the traffic of unneeded information by avoiding transferring the entire book contents, as conventional paper-based books do. Furthermore, the three-dimensional electronic atlases can be considered as a common index of multiple textbooks. In conventional indices, the key words are arranged alphabetically.

Therefore, the three-dimensional atlas, according to the present invention, is unique because; 1: the labels are arranged according to the 3D anatomical entities, which facilitate the reader interactions more intuitively and 2: it can more properly handle the notion of the anatomical scale; some anatomical names refer to structures of 10 cm scale, while some names refer to structures of 10 micron scale. It should also be noted that different fees can be charged for various levels of access to the three-dimensional atlas. Fees for information from the database in a "single serve" fashion could also be charged. Therefore, a user would not have to purchase access to the entirety of the three-dimensional database, but instead could purchase certain information and access on an as-needed basis.

In one embodiment, illustrated in FIG. 1, the system with a three-dimensional interface for interacting with a database can include a user interface device 10, and a remote database device 20. The user interface device 10 and the remote database device 20 may be a general computing device, such as a personal computer (PC), a UNIX workstation, a server, a mainframe computer, a personal digital assistant (PDA), smartphone, cellular phone, a tablet computer, a slate computer, or some combination of these. Alternatively, the user interface device 10 and the remote database device 20 may be a specialized computing device conceivable by one of skill in the art. The remaining components may include programming code, such as source code, object code or executable code, stored on a computer-readable medium that may be loaded into the memory and processed by the processor in order to perform the desired functions of the system.

Figure 2:
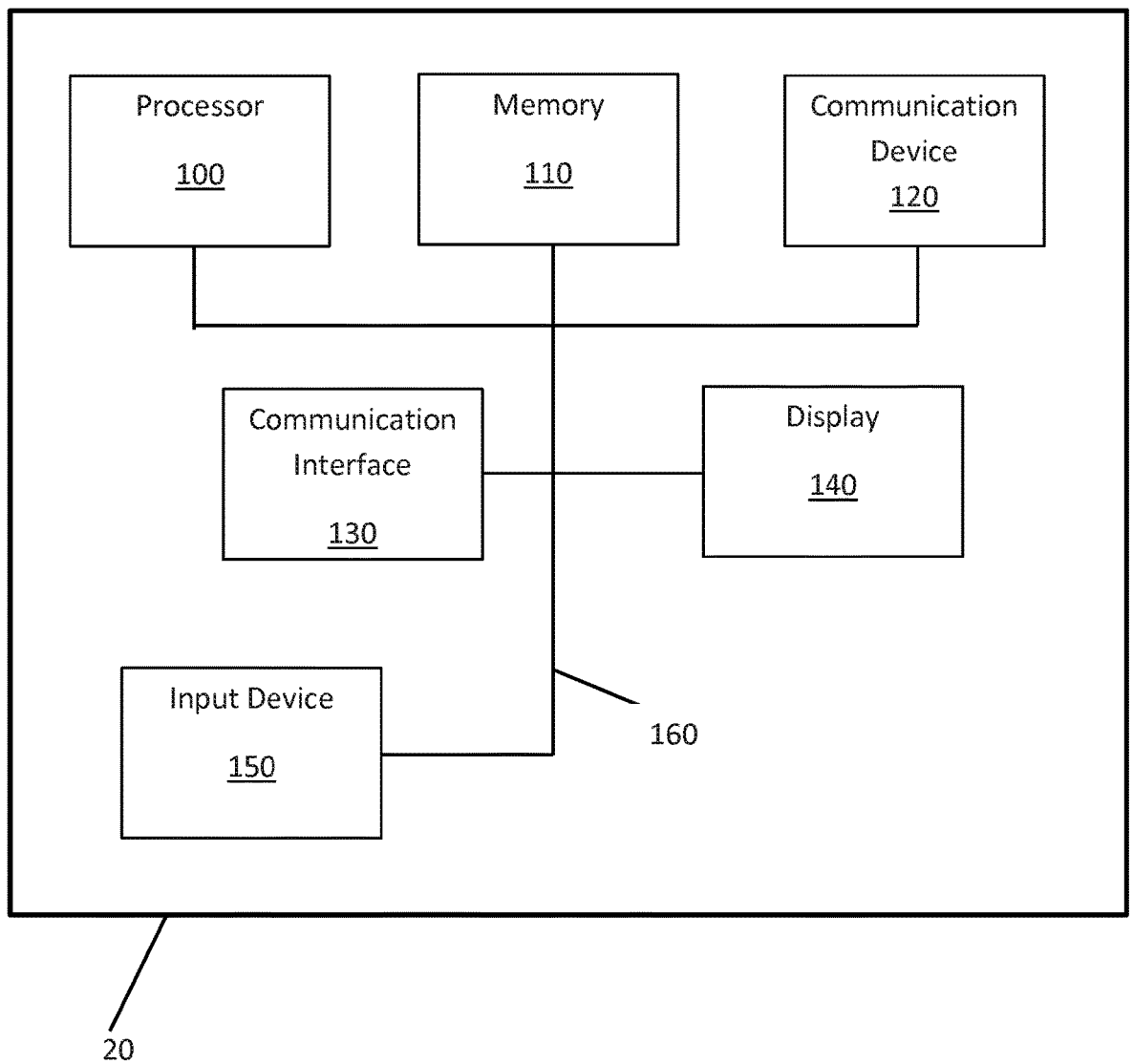
FIG. 2 illustrates a schematic view of a computing device for a system for interacting with a three-dimensional atlas and database according to an embodiment of the present invention.

The user interface device 10 and the remote database device 20 may communicate with each other over a communication network 30 via their respective communication interfaces as exemplified by element 130 of FIG. 2. The communication network 30 can include any viable combination of devices and systems capable of linking computer-based systems, such as the Internet; an intranet or extranet; a local area network (LAN); a wide area network (WAN); a direct cable connection; a private network; a public network; an Ethernet-based system; a token ring; a value-added network; a telephony-based system, including, for example, T1 or E1 devices; an Asynchronous Transfer Mode (ATM) network; a wired system; a wireless system; an optical system; cellular system; satellite system; a combination of any number of distributed processing networks or systems or the like.

Referring now to FIG. 2, the user interface device 10 and the remote diagnostic device 20 can each include a processor 100, a memory 110, a communication device 120, a communication interface 130, a display 140, an input device 150, and a communication bus 160, respectively. The processor 100, may be executed in different ways for different embodiments of each of the user interface device 10 and the remote database device 20. One option is that the processor 100, is a device that can read and process data such as a program instruction stored in the memory 110, or received from an external source. Such a processor 100, may be embodied by a microcontroller. On the other hand, the processor 100 may be a collection of electrical circuitry components built to interpret certain electrical signals and perform certain tasks in response to those signals, or the processor 100, may be an integrated circuit, a field programmable gate array (FPGA), a complex programmable logic device (CPLD), a programmable logic array (PLA), an application specific integrated circuit (ASIC), or a combination thereof. Different complexities in the programming may affect the choice of type or combination of the above to comprise the processor 100.

Similarly to the choice of the processor 100, the configuration of a software of the user interface device 10 and the remote database device 20 (further discussed herein) may affect the choice of memory 110, used in the user interface device 10 and the remote database device 20. Other factors may also affect the choice of memory 110, type, such as price, speed, durability, size, capacity, and reprogrammability. Thus, the memory 110, of user interface device 10 and the remote database device 20 may be, for example, volatile, non-volatile, solid state, magnetic, optical, permanent, removable, writeable, rewriteable, or read-only memory. If the memory 110, is removable, examples may include a CD, DVD, or USB flash memory which may be inserted into and removed from a CD and/or DVD reader/writer (not shown), or a USB port (not shown). The CD and/or DVD reader/writer, and the USB port may be integral or peripherally connected to user interface device 10 and the remote database device 20.

In various embodiments, user interface device 10 and the remote database device 20 may be coupled to the communication network 30 (see FIG. 1) by way of the communication device 120. In various embodiments the communication device 120 can incorporate any combination of devices—as well as any associated software or firmware—configured to couple processor-based systems, such as modems, network interface cards, serial buses, parallel buses, LAN or WAN interfaces, wireless or optical interfaces and the like, along with any associated transmission protocols, as may be desired or required by the design.

Working in conjunction with the communication device 120, the communication interface 130 can provide the hardware for either a wired or wireless connection. For example, the communication interface 130, may include a connector or port for an OBD, Ethernet, serial, or parallel, or other physical connection. In other embodiments, the communication interface 130, may include an antenna for sending and receiving wireless signals for various protocols, such as, Bluetooth, Wi-Fi, ZigBee, cellular telephony, and other radio frequency (RF) protocols. The user interface device 10 and the remote database device 20 can include one or more communication interfaces 130, designed for the same or different types of communication. Further, the communication interface 130, itself can be designed to handle more than one type of communication.

Additionally, an embodiment of the user interface device 10 and the remote database device 20 may communicate information to the user through the display 140, and request user input through the input device 150, by way of an interactive, menu-driven, visual display-based user interface, or graphical user interface (GUI). Alternatively, the communication may be text based only, or a combination of text and graphics. The user interface may be executed, for example, on a personal computer (PC) with a mouse and keyboard, with which the user may interactively input information using direct manipulation of the GUI. Direct manipulation may include the use of a pointing device, such as a mouse or a stylus, to select from a variety of selectable fields, including selectable menus, drop-down menus, tabs, buttons, bullets, checkboxes, text boxes, and the like. Nevertheless, various embodiments of the invention may incorporate any number of additional functional user interface schemes in place of this interface scheme, with or without the use of a mouse or buttons or keys, including for example, a trackball, a scroll wheel, a touch screen or a voice-activated system.

The different components of the user interface device 10 and the remote database device 20 can be linked together, to communicate with each other, by the communication bus 160. In various embodiments, any combination of the components can be connected to the communication bus 160, while other components may be separate from the user interface device 10 and the remote database device 20 and may communicate to the other components by way of the communication interface 130.

Some applications of the system for three-dimensional interface for interacting with a database may not require that all of the elements of the system be separate pieces. For example, in some embodiments, combining the user interface device 10 and the remote database device 20 may be possible. Such an implementation may be usefully where internet connection is not readily available or portability is essential.

Figure 3:
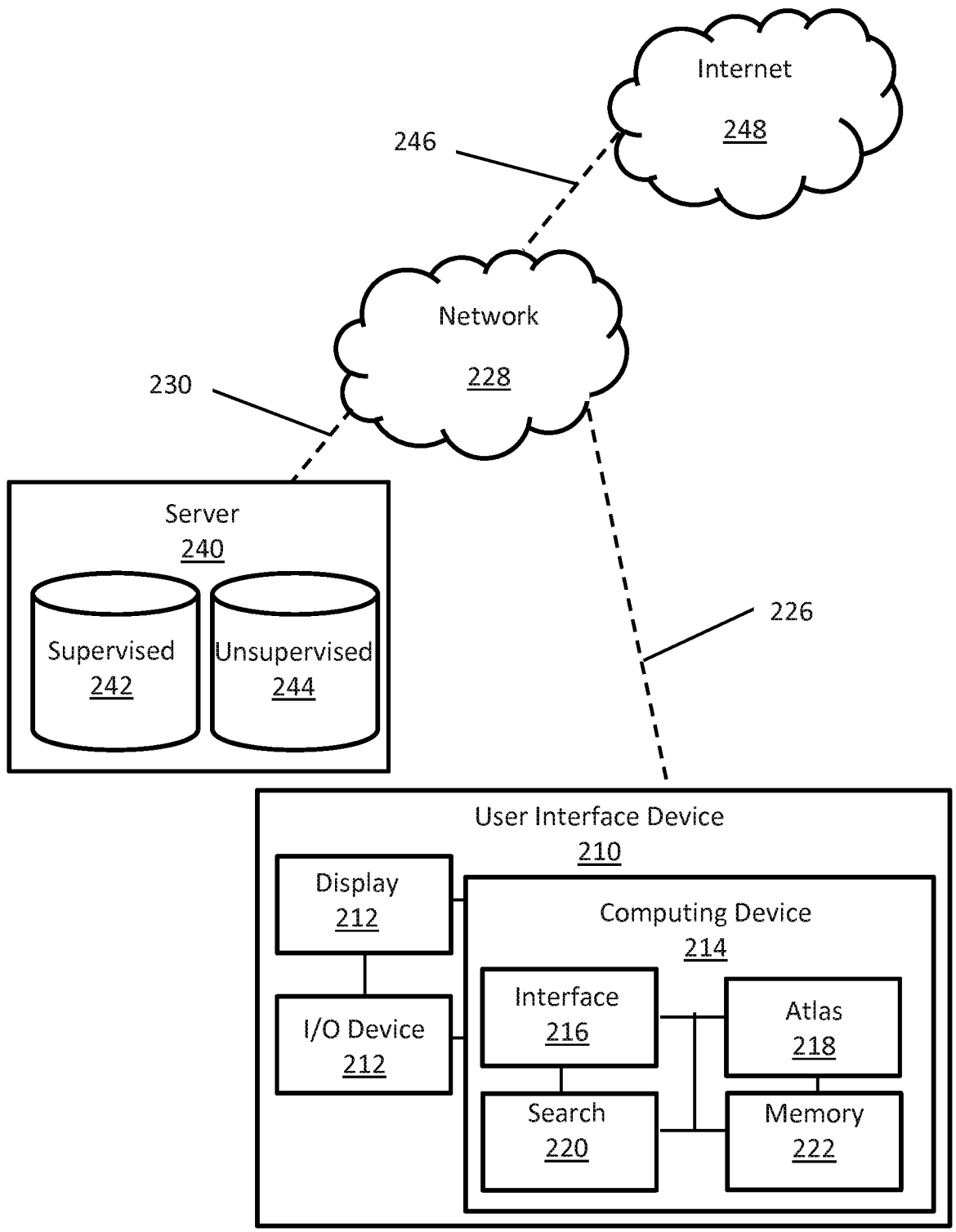
FIG. 3 illustrates a schematic diagram of the user interface, server, and network according to an embodiment of the present invention.

FIG. 3 illustrates a schematic diagram of the system 200 with a three-dimensional interface for interacting with a database according to an embodiment of the invention. The user interface device 210 includes a display 212, a computing device 214, and an input/output device 224. The computing device 214 contains programs, software, and/or an internet/intranet connection for displaying an user interface 216, a three-dimensional atlas 218, search interface 220 and memory 222. The computing device 212 is also configured to communicate via a first communication interface 226 with network 228. A second communication interface 230 which can be the same as first communication interface 226 allows for communication with server 240. Server 240 can contain one or both of a supervised database 242 and an unsupervised database 244. Alternatively, a third communications interface 246 can be used to communicate with the internet 248 to gather additional relevant information related to the desired topic.

More specifically, the interface 216 allows the user to interact with a three-dimensional atlas 218 representing the desired element of anatomy, machine, device, or other object via images shown on display 212 and input provided through the input/output device 224. The three-dimensional atlas 218 can include photographs, histology images, MR, CT and PET scan images, or any other source of images desired by or known to one of skill in the art. The three-dimensional atlas includes structure labels or coordinates for selecting specific areas of the atlased image to explore. The images in the three-dimensional atlas 218 can also be explored on different scales, such that areas that may not be apparent in a large scale atlas image may be revealed in smaller scale images.

When a user interacts with the atlas 218 and selects an area to explore the user can also search for additional information related to that area in the supervised and unsupervised databases 242 and 244. The user can review all information relevant to the area, or alternately, can do keyword searching within the articles, images, and other information contained in the database and associated with that area. Indeed, the information can also be organized in the database based on the areas to which it relates. The supervised database 242 can contain proprietary content and other content curated by the system provider. The unsupervised database 244 can reside on the server 240 with the supervised database 242 and can be filled with information provided by outside sources or found during manual or robotic searches of the internet. Alternately, the unsupervised database 244 can simply consist of an internet search executed by the program when a search is requested by the user.

Figure 4:
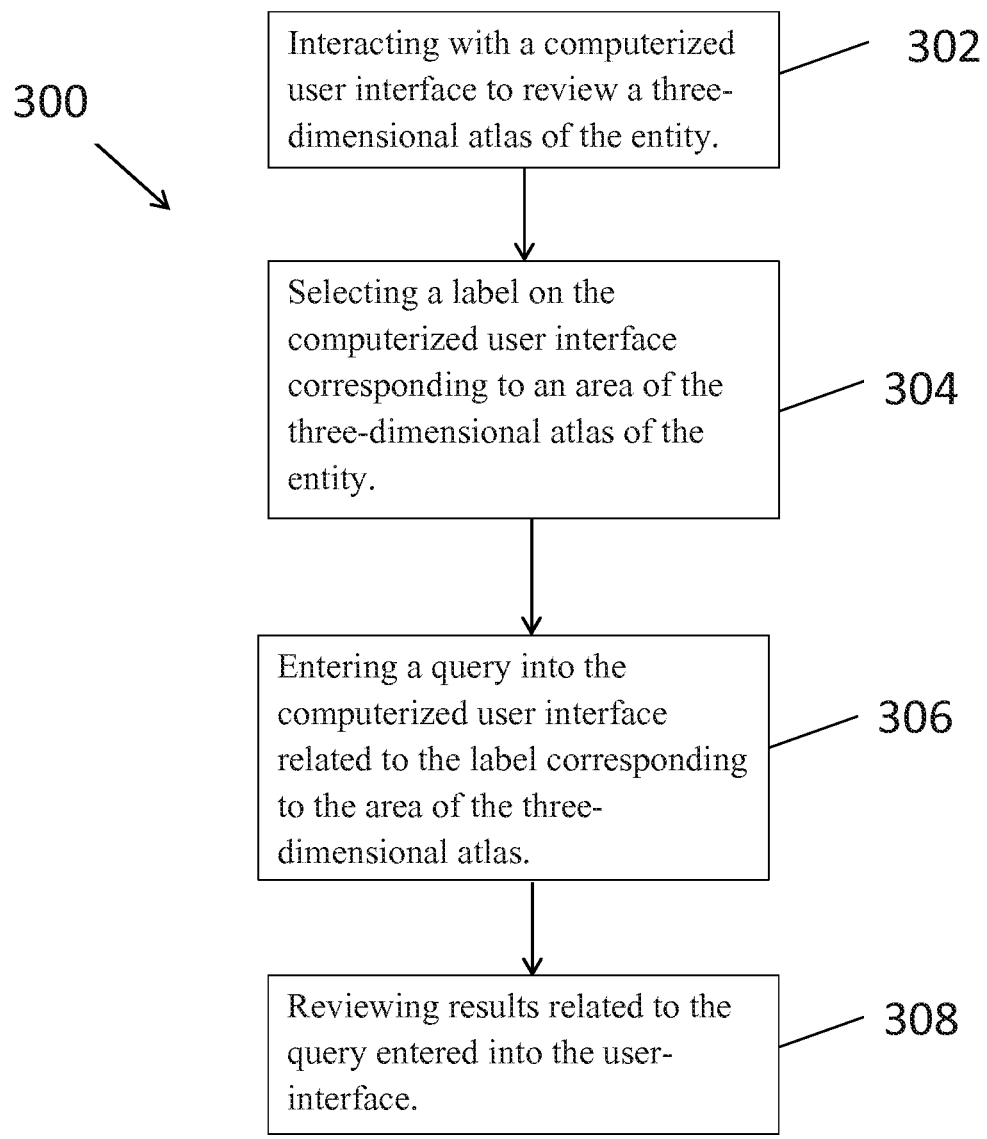
FIG. 4 illustrates a flow diagram of a method for searching for information related to an entity according to an embodiment of the present invention.

FIG. 4 illustrates a method for searching for information related to an entity. The method 300 includes step 302 of interacting with a computerized user interface to review a three-dimensional atlas of the entity. The method also includes step 304 of selecting a label on the computerized user interface corresponding to an area of the three-dimensional atlas of the entity. The method also includes step 306 of entering a query into the computerized user interface related to the label corresponding to the area of the three-dimensional atlas. Additionally, the method includes step 308 of reviewing results related to the query entered into the user-interface. The method can further include performing a key-word search related to the label corresponding to the area of the three-dimensional atlas.

EXAMPLE

An exemplary embodiment of the present invention directed to a three-dimensional brain atlas and interface for interacting with a database, is described below. This example is included merely to further illustrate the invention and is not meant to be considered limiting. While the exemplary embodiment is discussed with respect to a brain atlas, it is noted that any other element of anatomy, machine, device, or other suitable object could be mapped three dimensionally and used to provide the interface for interacting with the database, as would be known to one of skill in the art.

In the exemplary embodiment, the multi-scale electronic atlas of the brain is a three-dimensional and visual portal to a supervised and unsupervised knowledge databases. The supervised database will contain neuroscience textbooks and atlases. Through the visual interface of the electronic atlas, a user can identify structures of interest and can access to related histology panels, diagrams, and text information of the structures in the database. Namely, this electronic atlas will serve as an integrated, three-dimensional, and visual index of a large amount of publications. The atlas has an extensive gray and white matter, three-dimensional parcellation (more than 300 structures) in stereotaxic coordinates, and is available for use on personal tablet devices and can rely on cloud support.

In conventional atlases, the scale is predetermined and fixed. Many atlas books use histology sections, which have much higher resolution but the magnification of each panel is fixed. The exemplary brain atlas according to the present invention allows a user to interactively magnify or shrink each image, but the spatial resolution of the source images remains the same. A true multi-scale atlas consists of multiple image sources with different spatial resolutions. The tissue coverage of the higher resolution images is inevitably small and, therefore, they have to be arranged as a mosaic, using the lower resolution images as spatial guidance, which will preserve the stereotaxic coordinate system. This would lead to a huge amount of anatomical contents, only electronic formats can deliver.

For a multi-scale atlas, which consists of multiple image sources, each source needs to be three-dimensional to ensure accurate spatial registration among the sources and subsequent two-dimensional re-slicing with consistent anatomical angles. This can be achieved by three-dimensional micro-MR imaging (microMRI) of small postmortem tissue blocks. The local three-dimensional, high-resolution data can be registered in anatomically correct locations and orientations, keeping the consistent coordinates.

The role of conventional brain atlases is to define structures, locations, and names. However, the atlas according to the present invention defines a new potential of atlas as a portal to various types of databases. For example, the exemplary brain atlas according to the present invention includes approximately 300 names of structures and locations. Each name serves as a keyword to search databases through Internet. The exemplary brain atlas according to the present invention is linked to databases in Internet (PubMed, Science Direct, and BrainNavigator), which are examples of unsupervised databases. It should be noted that any other source of information known to one of skill in the art could also be used. An interface to supervised knowledge database is also included, and each name or coordinate defined in the atlas is linked to the wealth of information in the supervised database. The multi-scale approach is essential for the multi-content atlas because there are many anatomical definitions specific to each spatial scale; for example, the notion of the "corona radiata" can only be defined in the global map while definition of the "inferior olive nucleus" requires a high-resolution map.

The contents of the exemplary interface and database can be housed on a centralized server, however the setup of the interface and database can be anything known to or conceivable by one of skill in the art. With the Cloud approach, the information is transferred on-demand, rather than transferring the entire data at once to the local system. The addition and management of new knowledge becomes far simpler and traffic of copyrighted products can be monitored, providing an ideal business platform.

Figure 5:
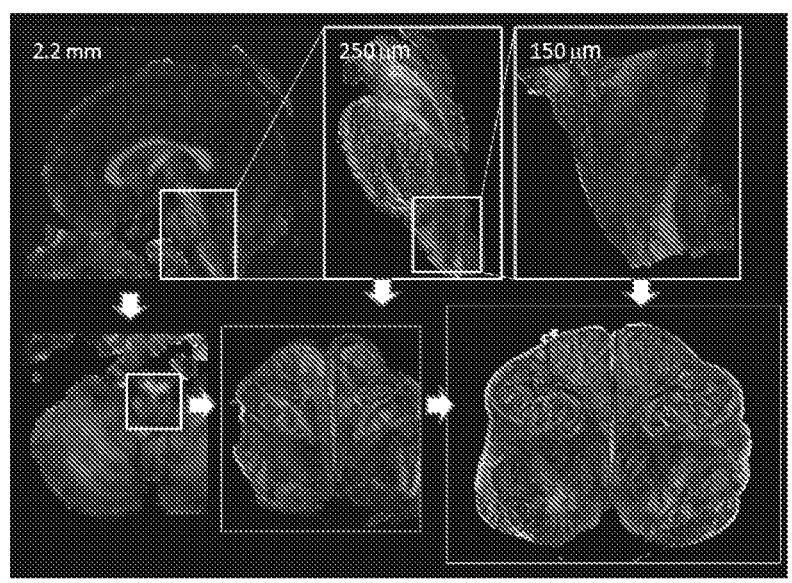
FIG. 5 illustrates an example of multi-scale anatomical information and structural notions at different scales.

FIG. 5 illustrates an example of multi-scale anatomical information and structural notions at different scales. The 2.2-mm in vivo MRI in iPad Atlas provides macroscopic information about the location of the medulla in relation to the pons, the spinal cord, and the cerebellum. The 250 µm micro-MRI of a postmortem sample was obtained from a horizontal animal scanner and registered to the exemplary brain atlas, providing a higher-resolution view. A smaller postmortem sample was scanned by a vertical NMR, providing 100 µm views of the anatomy, revealing even smaller structures.

The expertise and resources for micro-imaging is a key for the multi-scale atlas. It is straightforward to provide magnification of an image. However, the true multi-scale atlas should integrate data with different spatial resolutions, as illustrated in FIG. 5. Conventional in vivo three-dimensional MRI, which is used for the exemplary brain atlas according to the present invention, is capable of defining macroscopic structures three-dimensionally with high anatomical fidelity without distortion and damages to the brain. While typical human scanners can provide image resolution in the order of 1 mm, microMRI of postmortem tissues can provide image resolution up to 40 µm. To create an image of the human brain with 100 µm resolution, the image matrix size become approximately 14 GB for the entire brain. In the future, to extend the resolution to 50 µm as routinely done for rodent MRI, the data size would reach 100 GB. In addition, the probe size for microMRI becomes smaller as the resolution goes higher. For example, a horizontal 11.7T MRI scanner can accommodate samples up to 10 cm. The vertical 11.7T NMR has much higher gradient strength and can deliver higher resolution but the largest probe is 3 cm. The limitations in the probe and image matrix sizes suggest that the high-resolution imaging inevitably have to be based on a portion of the brain and the coordinates of each brain tissue needs to be registered to the global three-dimensional coordinates defined in the exemplary embodiment of the brain atlas according to the present invention. This can be most accurately done by three-dimensional imaging followed by elastic image registration.

Figure 6:
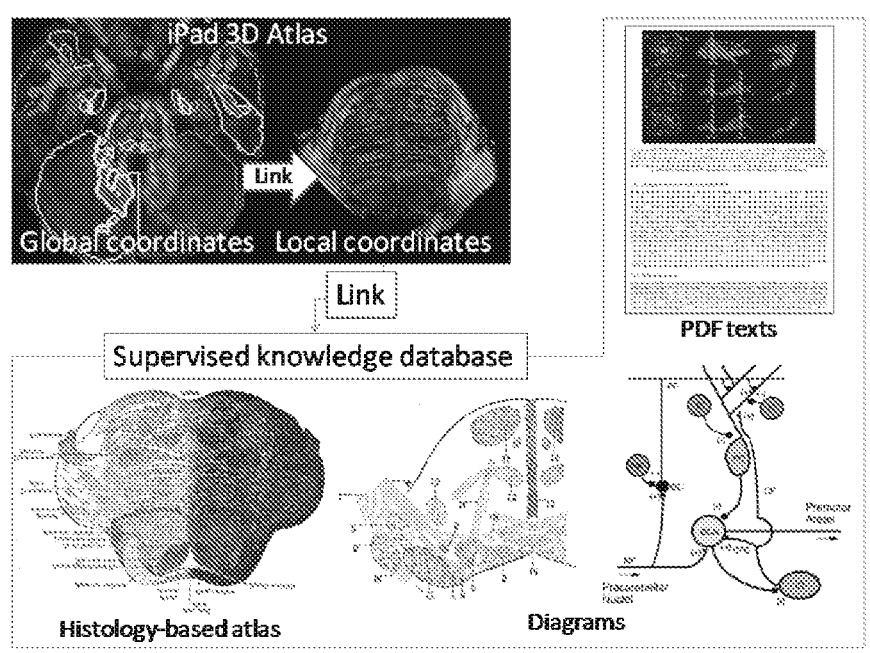
FIG. 6 illustrates a link between a three-dimensional atlas and a supervised atlas according to an embodiment of the present invention.

The exemplary brain atlas is enriched with a supervised knowledge database. The multi-scale dimension enhances the capability as the multi-dimensional portal system, as illustrated in FIG. 6. Supervised information can come from books and articles or any other source known to one of skill in the art.

Figures 7A, 7B, 7C, 7D, 7E:
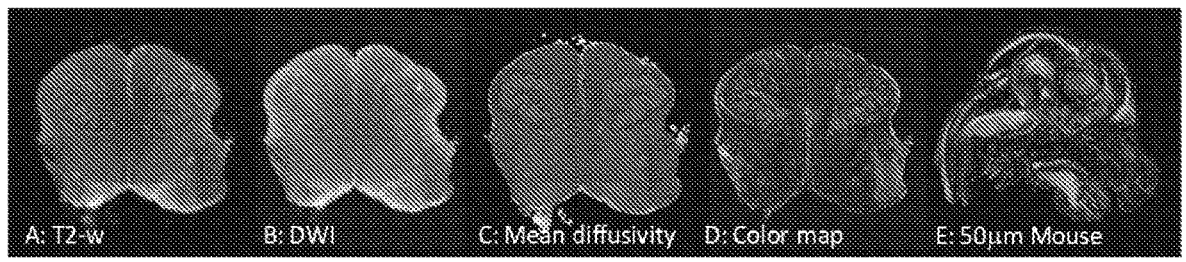
FIGS. 7A-7E illustrate multiple MRI/DTI contrasts at 150 μm, revealing different types of structures based on local cellular architectures according to an exemplary embodiment of the present invention.

Micro MR imaging, especially super-high-resolution diffusion tensor imaging (DTI), is used to provide the exemplary brain atlas. The microMRI/DTI provides multiple image contrasts including T2-weighted, diffusion-weighted, mean diffusivity, fractional anisotropy, and color-coded structural orientation maps (color map). Among these images, the DTI-derived color map carries by far the largest amount of anatomical information, as illustrated in FIGS. 7A-7E. FIGS. 7A-7E illustrate multiple MRI/DTI contrasts at 150 µm, revealing different types of structures based on the local cellular architectures. FIG. 7A illustrates a T2-weighted image. FIG. 7B illustrates a diffusion-weighted image. FIG. 7C illustrates a mean diffusivity image. FIG. 7D illustrates a color-coded orientation map, and FIG. 7E illustrates an example of 50 µm mouse embryo DTI data.

The relaxation-weighted and diffusion-weighted images simply do not have enough contrast to decipher various microscopic anatomical entities. It is widely believed that diffusion anisotropy and tissue-orientation based contrasts are useful only for white matter structures. This is the case when image resolution is low relative to the complicated gray matter structures. As shown in FIGS. 5, 6, and 7A-7E many gray matter structures have characteristic diffusion anisotropy and tissue orientation and, thus, can be delineated by DTI clearly. To create the exemplary brain atlas postmortem brain samples are scanned as 5-10 cm blocks for 250 µm resolution. The samples are further sectioned to 2-3 cm blocks for 150 µm and higher resolution, covering many important brain structures at multiple resolutions.

Once high-resolution MR images of a small tissue block are obtained, they need to be registered to the three-dimensional global coordinates as shown in FIG. 5. CBIS developed MriStudio (www.mristudio.org), an image visualization, transformation, and registration software. This software allows users to have an access to a cutting-edge image transformation algorithm running in IBM iDataPlex 2,000 core computer through a Cloud-type remote analysis technique. The three-dimensional-to-three-dimensional multi-scale image registration described with respect to the exemplary brain atlas is based on this technology. However, any other suitable technology known to or conceivable by one of skill in the art could also be used. More specifically, the technique is based on Large Deformation Diffeomorphic Metric Mapping (LDDMM), developed by Dr. Miller and the MriStudio interface allows landmark-based initial elastic warping, followed by three-dimensional volume-based image-to-image elastic mapping.

Because the size of the supervised knowledge database is expected to grow rapidly with a large amount of high-resolution histology panels, diagrams, and texts, it is more practical to host the entire knowledge database in a centralized server and provide them upon request, rather than transferring the entire database to each device at the time of purchase. This Cloud approach has a distinctive advantage when constantly updating the database with only one copy of the database.

The Master Atlas can be, for example, the whole brain atlas is widely known as Eve atlas and used for atlas-based three-dimensional image analysis as a part of the packages of commonly used image analysis software such as FSL, Slicer3, and MriStudio. This is used as a Master Atlas to which all future multi-scale atlases is registered. The multi-scale data in this example is based on the existing high-resolution MRI/DTI of a brainstem. Briefly, DTI of the whole brainstem was performed on a horizontal 11.7 T NMR spectrometer, using a 12-shot three-dimensional diffusion-weighted echo planar imaging (EPI) sequence (TE/TR=27/500 ms, 1 signal average). The imaging field-of-view and matrix size were 43×43×65 mm$^3$ and 168×168×256, respectively, to give an isotopic spatial resolution of 255×255×255 $\mu m^3$. Two b0 images and 30 diffusion-weighted images were acquired with a total scan time of 13.5 h. The cervical spinal cord was imaged on a vertical bore 11.7 T scanner using a 20-mm diameter RF coil. A three-dimensional diffusion-weighted gradient and spin echo (DW-GRASE) sequence with twin-navigator echo phase correction was used (TE/TR=32/800 ms, $\delta/\Delta$=3/15 ms, 4 signal averages). The imaging field-of-view and matrix size were 16×12.5×17.2 mm$^3$ and 128×100×138, respectively, to give an isotopic spatial resolution of 125×125×125 $\mu m^3$. For DTI diffusion-weighted imaging directions were acquired with a total scan time of 18 h. The medulla was imaged on a vertical bore 11.7 T scanner, using a 30 mm diameter RF coil. A three-dimensional diffusion-weighted multiple spin echo sequence was used for DTI (TE/TR=34/400 ms, $\delta/\Delta$=3/15 ms, 2 signal averages). The imaging field-of-view and matrix size were 30×26×24.6 mm$^3$ and 176×152×144, respectively, to give an isotropic resolution of 170×170×170 $\mu m^3$. Six diffusion-weighted directions were acquired, with a total scan time of 37 h.

All image alignment for the exemplary atlas was performed by MriStudio (www.mristudio.org). The initial alignment is based on rigid transformation driven by manually placed landmarks. Approximately 20 landmarks are placed on clearly identifiable anatomical landmarks both in whole brain atlas and the brainstem high-resolution images. This registers the images from a tissue section to the whole-brain atlas. The tensor information will require a proper tensor re-orientation method, which is already implemented in MriStudio. After the initial alignment, the section of the Master Atlas that correspond to the ex vivo tissue is cropped for the final elastic registration. The volume-based three-dimensional image-to-image matching is based on dual-channel LDDMM using FA and trace maps. After the transformation, the transformation matrix is applied to the tensor map, from which DTI-derived scalar maps is created.

The exemplary brain atlas contains 15 axial, 15 coronal, and 9 sagittal panels that contain the brainstem area. 39 corresponding high-resolution panels are generated and segmented/annotated using the same multi-layer architecture. As the high-resolution images are multi-contrast data with T2-weighted, diffusion-weighted, diffusion-constant map, and orientation-coded anisotropy map (color map), the number of panels will be 39×4 contrasts=156 panels, the superimposing annotation and segmentation files are layer structures and thus can be shared by all images with different contrasts. The anatomical nomenclature of Paxinos&Huang brainstem atlas is used. However, any other suitable nomenclature known to or conceivable by one of skill in the art could also be used.

High-resolution imaging can also be performed for other various brain structures. These can include, but are not limited to, all deep gray matter structures (lenticular nuclei, caudate, thalamus, hypothalamus, hippocampus, and amygdala) and representative cortical areas. For the brainstem, 250 and 150 m data are available and will proceed to 50 $\mu m$ data for complicated reticular formation areas. These three-dimensional objects will all be registered to the Master atlas, resliced to the standard axial, coronal, and sagittal panels, segmented, and annotated. In addition, currently the two-dimensional panels are available for only 2.5 mm intervals, which is extended to 1 mm intervals.

Although the multi-scale data is all three-dimensional, the atlas could be based on sliced two-dimensional panels in three standard orientations. Usually, the most difficult and time-consuming step for a three-dimensional extension is to define objects in the three-dimensional space, which requires extensive manual delineation. In the Master Atlas, more than 200 volume structures and more than 90 white matter three-dimensional streamline objects are defined based on more than 10 years of work of human atlas project (RO1 AG20012, "Human White Matter Tract Mapping by Diffusion MRI). The visualization interface of MriStudio was developed by PI (Hangyi Jiang), which can present these objects using tri-plane, surface rendering, and streamline based on OpenGL. These programs and objects will be transplanted to XCODE environment for iPad and other types of portable devices. Incorporation of the high-resolution data for three-dimensional visualization can also be used with remote three-dimensional rendering.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

What is claimed is:

1. A system for providing and retrieving information related to a three-dimensional part of anatomy comprising:
a hardware processor;
a non-transitory computer readable medium programmed with a navigable and manipulatable three-dimensional atlas depicting the three-dimensional part of anatomy, such that a user can interact with imaging of the three-dimensional part of anatomy, wherein the three-dimensional atlas includes a plurality of labels to describe the three-dimensional part of the anatomy, wherein the plurality of labels comprise a first label for the three-dimensional part of the anatomy for a first scale and a second label that is different than the first label for the three-dimensional part of the anatomy at a second scale that is different than the first scale and the three-dimensional atlas comprises a plurality of high resolution images of the part of the anatomy generated using micro-magnetic resonance imaging, wherein the micro-magnetic resonance imaging comprises diffusion tensor imaging and the plurality of labels for selecting specific areas to explore and wherein the high resolution images are registered to three-dimensional global coordinates such that there is three-dimensionalto-three dimensional registration of components of the part of the anatomy on different scales, and wherein the three-dimensional atlas includes multiple three-dimensional image sources of the part of the anatomy with different spatial resolutions, and wherein the three-dimensional atlas is configured to allow the user to interactively magnify or shrink each image while a spatial resolution of the multiple three-dimensional image sources remains the same;

wherein the non-transitory computer readable medium is further programmed to communicate with a multi-content knowledge database containing the information related to the three-dimensional part of the anatomy, wherein the database includes multiple entries, wherein the information in each of the entries is categorized relative to the plurality of labels, wherein the information relative to the plurality of labels, including image information, is converted into text and numbers, such that the information can be searched throughout the multiple entries in the database, and wherein the information is transmitted from the database on demand, and wherein the plurality of labels is linked to relevant information in the multi-content knowledge database to provide the user with information for a three-dimensional part of the anatomy of interest to the user;

a user interface device, wherein the user interface device is used in conjunction with the non-transitory computer readable medium and the navigable and manipulatable three-dimensional atlas depicting the three-dimensional part of anatomy to provide an interface for searching the database using the plurality of labels and navigation and manipulation of the three-dimensional atlas depicting the three-dimensional part of anatomy to find the plurality of labels within the three-dimensional atlas, configured such that the user can select a one of the plurality of labels from the three-dimensional atlas to search the database and the interface returns search results categorized relative to the one of the plurality of labels in the database, and wherein the user can interact with the three-dimensional atlas to zoom in on particular areas, view the particular areas with specificity, find the plurality of labels at different scales of the atlas, identify a different one of the plurality of labels at different scales of the atlas, and perform searches of the multi-content knowledge database from the plurality of labels of the three- dimensional part of the anatomy of interest to the user, wherein certain ones of the plurality of labels are only viewable at particular scales of the atlas;

a display configured to show the user the three-dimensional atlas depicting the part of the anatomy and the one of the plurality of labels, such that the user can select the one of the plurality of labels using the interface, and wherein the display is also configured to display the search results categorized relative to the one of the plurality of labels; and wherein the non-transitory computer readable medium programmed with the three-dimensional atlas, the database, and the interface are programmed onto at least one computing device.

2. The system of claim 1 further comprising said part of the anatomy being an element of anatomy.

3. The system of claim 1 wherein the three-dimensional atlas comprises images and said images consist of at least one selected from a group of magnetic resonance imaging (MRI) images, histology images, PET-scan images, and CAT-scan images.

4. The system of claim 1 wherein the one of the plurality of labels is a spatial coordinate.

5. The system of claim 1 wherein the one of the plurality of labels is a designation for an anatomical structure.

6. The system of claim 1 wherein the interface is configured such that the user can search within the information categorized relative to the one of the plurality of labels in the database.

7. The system of claim 1, wherein the interface is configured for the user to perform a keyword search of the database.

8. The system of claim 1, wherein the database comprises a supervised database and an unsupervised database.

9. The system of claim 8, wherein the unsupervised database is built from information available on the internet.

10. A system for retrieving information related to a brain comprising:

a non-transitory computer readable medium programmed with a navigable and manipulatable three-dimensional atlas depicting the brain such that a user can interact with the three-dimensional atlas depicting the brain, wherein the three-dimensional atlas includes plurality of labels, wherein the plurality of labels comprise a first label for the three-dimensional part of the anatomy for a first scale and a second label that is different than the first label for the three-dimensional part of the anatomy at a second scale that is different than the first scale and wherein the three-dimensional atlas comprises high resolution magnetic resonance (MR) images generated using micro magnetic resonance imaging and the plurality of labels for selecting specific areas to explore, wherein the micro magnetic resonance imaging takes the form of diffusion tensor imaging, wherein the high resolution MR images are scanned as 5-10 cm blocks for 250 pm resolution and further sectioned to 2-3 cm blocks for 150 pm and greater resolution, and wherein the high resolution MR images are transformed and registered to three-dimensional global coordinates such that there is three-dimensional-to-three dimensional registration of components of the brain on different scales, and wherein said three-dimensional atlas is configured for the user to interact with the atlas at multiple scales, and wherein the three-dimensional atlas includes multiple three-dimensional image sources with different spatial resolutions, and wherein the three-dimensional atlas is configured to allow the user to interactively magnify or shrink each image while a spatial resolution of the multiple three-dimensional image sources remains the same;

a multi-content knowledge database containing the information related to the brain, wherein the database includes multiple entries wherein the information in each of the entries is categorized relative to the plurality of labels, wherein the information relative to the plurality of labels, including image information, is converted into text and numbers, such that the information can be searched throughout the multiple entries in the database, and wherein the contents of the database can be transferred on demand, and wherein the plurality of labels is linked to relevant information in the multi-content knowledge database to provide the user with information for a three-dimensional brain of interest to the user;

a user interface device, wherein the user interface device is programmed to provide an interface for searching the database using the plurality of labels and the navigable and manipulatable three-dimensional atlas depicting the brain, configured such that a user can select a one of the plurality of labels from the three-dimensional atlas to search the database and the interface returns search results categorized relative to the one of the plurality of labels in the database, and wherein the user interface device is configured to allow the user to interact with the three-dimensional atlas on different scales, and wherein the user can interact with the three-dimensional atlas to zoom in on particular areas, view the particular areas with specificity, find the plurality of labels at different scales of the atlas, identify a different one of the plurality of labels at different scales of the atlas, and perform searches of the multi-content knowledge database from the plurality of labels of the three-dimensional brain of interest to the user, wherein certain ones of the plurality of labels are only viewable at particular scales of the atlas;

a display configured to show the user the three-dimensional atlas depicting the brain and the one of the plurality of labels, such that the user can select the one of the plurality of labels using the interface, and wherein the display is also configured to display the search results categorized relative to the one of the plurality of labels; and wherein the non-transitory computer readable medium programmed with the three-dimensional atlas, the database, and the interface are programmed onto at least one computing device.

11. The system of claim 10 wherein the three-dimensional atlas comprises images and said images consist of at least one selected from the group of magnetic resonance imaging (MRI) images, histology images, PET-scan images, and CAT-scan images.

12. The system of claim 10 wherein the one of the plurality of labels is a spatial coordinate.

13. The system of claim 10 wherein the one of the plurality of labels is a designation for a structure within the brain.

14. The system of claim 10 wherein the interface is configured such that the user can search within the information categorized relative to the one of the plurality of labels in the database.

15. The system of claim 10, wherein the database comprises a supervised database and an unsupervised database.

16. The system of claim 15, wherein the unsupervised database is built from information available on the internet.

17. The system of claim 15 wherein the supervised database further comprises information in an electronic format such as text, books, pictures, photographs, or clinical images.

18. The system of claim 17 wherein the label is linked to at least a portion of the information in the supervised database and the requested information related to the label is transferred to the user.

19. The system of claim 17 further comprising the information being pre-transferred to a local computer or remain in a centralized server and transferred upon request.

20. The system of claim 17 further comprising the information residing on a centralized server and transferred upon request.

21. The system of claim 10 wherein the three-dimensional atlas comprises multiple spatial scales for comprehensive listing of anatomical names with different spatial scales.

* * * * *